United States Patent [19]
George

[11] Patent Number: 5,524,306
[45] Date of Patent: Jun. 11, 1996

[54] BED RESTRAINT

[76] Inventor: Hector M. George, 4011 Toledo St., Coral Gables, Fla.

[21] Appl. No.: 377,837

[22] Filed: Jan. 25, 1995

Related U.S. Application Data

[63] Continuation-in-part of Ser. No. 246,637, May 20, 1994, abandoned.

[51] Int. Cl.⁶ .................................................. A47C 21/08
[52] U.S. Cl. .................................. 5/424; 5/658; 5/505.1; 128/869
[58] Field of Search .................................. 5/97, 424, 425, 5/494, 505.1, 658, 628, 88.1; 128/869, 872

[56] References Cited

U.S. PATENT DOCUMENTS

| | | |
|---|---|---|
| 2,774,079 | 12/1956 | Flatley . |
| 2,883,678 | 4/1959 | Heffernan et al. . |
| 3,099,842 | 8/1963 | Jensen . |
| 3,546,721 | 12/1970 | Cleary . |
| 4,074,375 | 2/1978 | Kella . |
| 4,180,879 | 1/1980 | Mann . |
| 4,214,328 | 7/1980 | Custer, Jr. et al. . |
| 4,653,131 | 3/1987 | Diehl . |
| 4,742,821 | 5/1988 | Wootan . |
| 5,027,456 | 7/1991 | Wadsworth . |
| 5,070,557 | 12/1991 | Vincent et al. . |
| 5,094,251 | 3/1992 | Miller . |
| 5,097,550 | 3/1992 | Marra, Jr. . |
| 5,153,954 | 10/1992 | Ohman . |

Primary Examiner—Michael F. Trettel
Attorney, Agent, or Firm—Larson and Taylor

[57] ABSTRACT

A bed restraint for helping to keep a person with diminished capacities in bed without restricting the person's normal sleeping movements includes an elongate base having opposed lateral edges. At least one flexible flap extends laterally from each of the lateral edges and terminates at a free end. The flap extends around a top member of the associated side of the bed and back against the base. A first fastening device fastens the free end of each flap to the base so that the base is suspended above the mattress and person to prevent upwards movement by the person in getting out of the bed. In the preferred embodiment, the bed restraint further includes a cover member or second flap with an associated second fastening device for covering the first fastening device so that the person will not easily be able to unfasten the first fastening device even if so inclined. This second fastening device is then located near the base of the bed, away from where the person could easily reach it. Alternatively, the cover member is attached along part of the longitudinal edges and across the base so as to form a pocket covering the first fastening device and may further include members for closing the pocket. According to the preferred embodiment, the base, the flaps, and the cover member are made of cloth and stitched together, and the fastening devices include buttons and button holes. Further, a bridging member is located along the longitudinal edges to prevent the centers of the longitudinal edges from sagging excessively and onto the person.

22 Claims, 2 Drawing Sheets

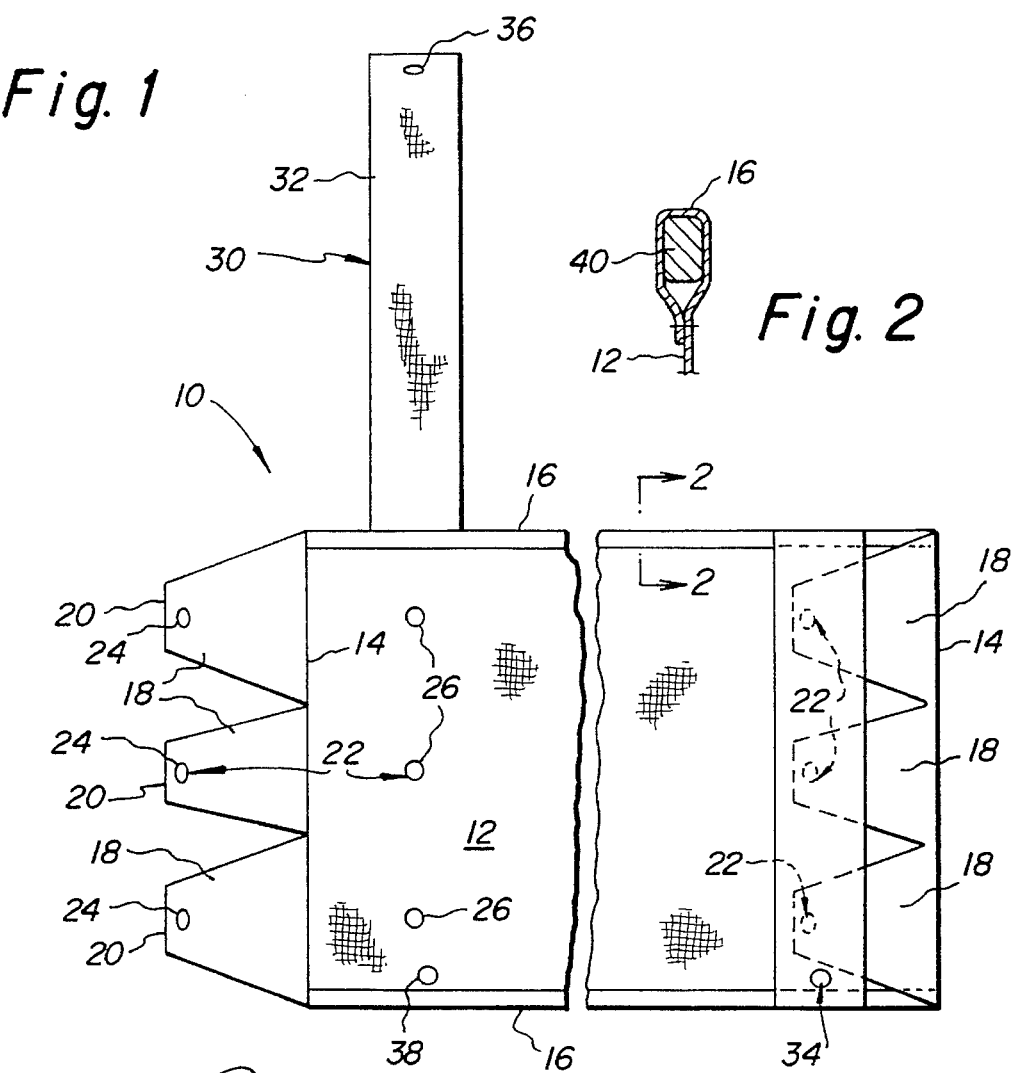
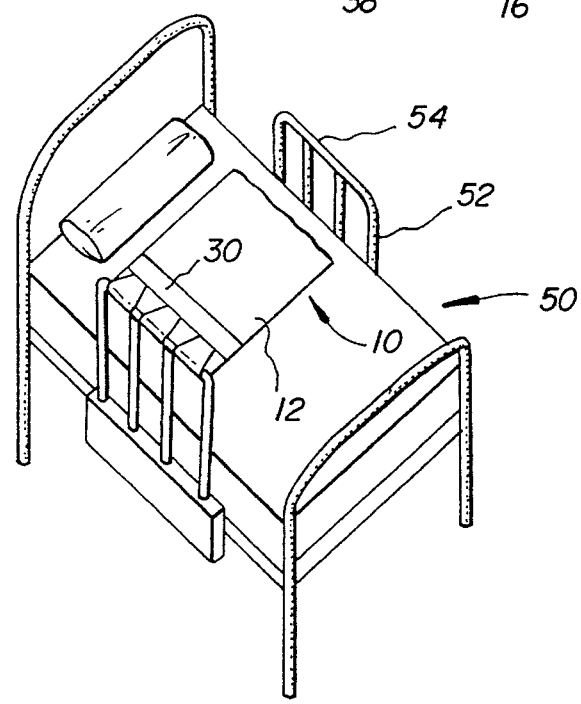

BED RESTRAINT

RELATED APPLICATIONS

This is a continuation-in part of U.S. application Ser. No. 08/246,637 filed May 20, 1994 now abandoned.

FIELD OF THE INVENTION

The present invention relates generally to an apparatus for helping to keep a person in bed, and more particularly to an apparatus which is positioned above the person and which cannot be easily removed by a person having diminished capacities.

BACKGROUND OF THE INVENTION

When a person suffers from certain disorders, brain syndromes, or the like, it is sometimes desirable to prevent that person from easily getting out of bed once that person is put into bed by an attendant, especially at night. This occurs both in hospital as well as home settings. Such a restraint is necessary to prevent the person from getting out of bed while the attendant is elsewhere, as such a person might fall and hurt themselves.

While systems to restrain a person in a bed are known in the prior art, such systems typically engage the person—as by tying the hands or other body parts to the bed. Such systems are uncomfortable at best, and often unduly restrict the normal and expected movements of the sleeping person.

SUMMARY OF THE INVENTION

In accordance with the present invention, a bed restraint for helping to keep a person on a mattress of a bed without restricting the person's normal sleeping movements is provided. The bed includes upstanding sides having a distinct top member above the mattress. The restraint then includes an elongate base having opposed lateral edges, with the lateral edges extending longitudinally along respective ones of the top members of the sides of the bed. At least one flexible flap extends laterally from each of the lateral edges and terminates at a free end. The flap extends around the top member of the associated side and back against the base with the free end in contact with the base. Then, a first fastening means fastens the free end of each flap to the base after the flap is passed around the top member so that the base is suspended above the mattress. In this position, the base is located just above the person and out of the way of the person's typical sleep movements. However, should the person attempt to get out bed, the person will not be able to move upwards very far before the base prevents further movement and hence getting out of the bed.

In the preferred embodiment, the bed restraint further includes a cover member for covering the first fastening means so that the first fastening means are hidden and not easily unfastened. In this manner, the person will not easily be able to unfasten the first fastening means even if so inclined. To help to assure this, a second fastening means is also included for fastening the cover member to the base over the first fastening means. This second fastening means is then located near the base of the bed, away from where the person could easily reach it. Alternatively, the cover member is attached to longitudinal edges of the base and across the base to form a pocket covering the first fastening means. Such a cover member may also include a device for closing the pocket formed thereby.

According to the preferred embodiment, the base includes opposed longitudinal edges spanning the lateral edges and the cover member is a respective flexible second flap for each first fastening means. Each second flap is attached to an associated one of the longitudinal edges so as to be positionable over the respective first fastening means. The second fastening means then fastens the second flaps to the base. Each respective second flap also covers the associated free end when the second flap is fastened to the base.

In the most preferred embodiment, the base, the flaps, and the cover member are made of cloth and stitched together. In addition, the first fastening means and the second fastening means include a button and button hole. Further, there are three of the flexible flaps extending laterally from each of the lateral edges.

It will be appreciated that the base includes opposed longitudinal edges spanning the later edges. It is a further feature of the present invention that a bridging member is located along these longitudinal edges. This bridging member prevents the centers of the longitudinal edges from sagging excessively and onto the person as the lateral edges are supported by the top members of the sides of the bed.

It is an object of the present invention to provide a bed restraint which is comfortable to the person being restrained.

It is also an object of the present invention to provide a bed restrict which is easy to mount and demount by an attendant, but which is not easy to demount by a person being restrained who has diminished capacities.

It is a further object of the present invention to provide a bed restraint which is usable with a variety of beds.

Other features, objects and advantages of the present invention are stated in or apparent from detailed descriptions of presently preferred embodiments of the invention found hereinbelow.

BRIEF DESCRIPTION OF THE DRAWINGS

FIG. 1 is a top plan view of the bed restraint of the present invention.

FIG. 2 is a cross-sectional view of the edge depicted in FIG. 1 taken along the line 2—2.

FIG. 3 is a top perspective view of a bed provided with the bed restrain depicted in FIG. 1.

DETAILED DESCRIPTION OF THE PREFERRED EMBODIMENTS

Figure 4:
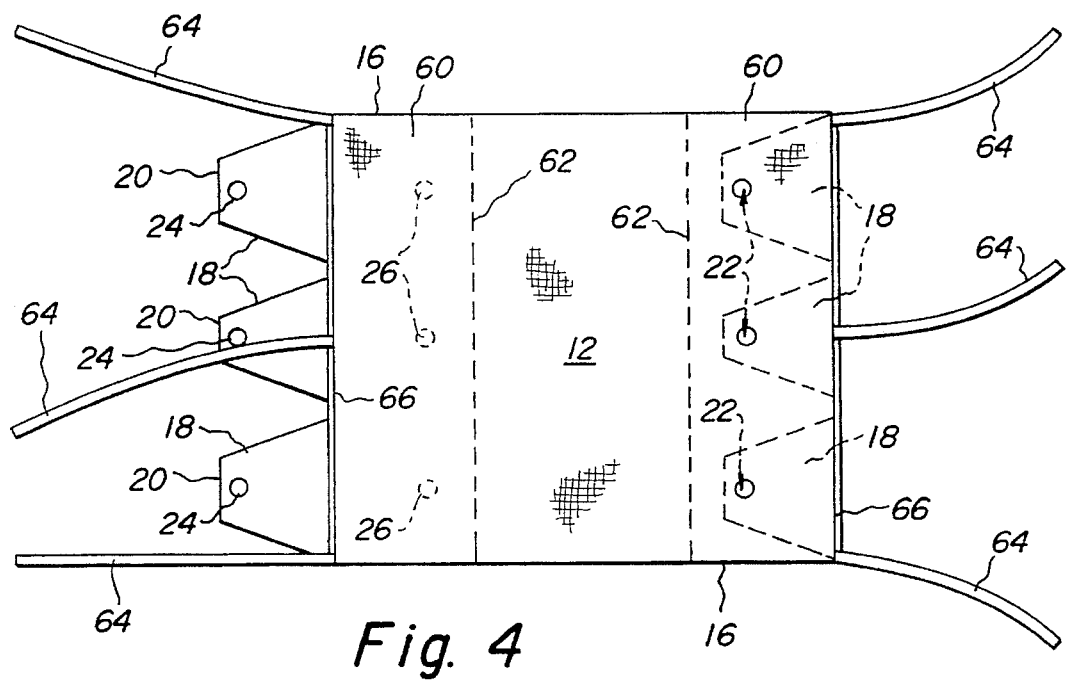
FIG. 4 is a top plan view of an alternative embodiment of the bed restraint of the present invention.

With reference now to the drawings in which like numerals represent like elements throughout the views, a bed restraint 10 is depicted in FIG. 1 with the various elements of the left side opened up and those of the right side closed over. Bed restraint 10 is preferably primarily made of cloth or the like which has been stitched together, although those of ordinary skill will appreciate that various other materials and fabrication techniques are possible such as plastic and one-piece construction.

Bed restraint 10 includes an elongate base 12 having opposed lateral edges 14 and longitudinal edges 16. Extending laterally from each lateral edge are three flexible flaps 18 (shown extending on the left side of FIG. 1 and folded over on the right side). While greater or lesser numbers of flaps 18 are possible, three is preferable to this embodiment as conforming with the number of openings in the side rail of a (Fowler or other such) bed to which bed restraint 10 is to be attached (as explained subsequently). Each flap 18 includes a free end 20 which is designed to be folded over onto base 12 and attached thereto by a first fastening means 22. Conveniently, first fastening means 22 includes a button hole 24 provided at each free end 20 and a button 26 sewn to base 12 as shown. Obviously, other suitable fastening means are usable in place of the disclosed fastening means, such as hook and latch (Velcro) type elements, zippers, or the like.

Preferably, bed restraint 10 also includes a cover member 30 for covering first fastening means 22 once flaps 18 are secured in place on top of base 12. In this embodiment, cover member 30 is a pair of second flaps 32 attached to the longitudinal edge 16 which will be nearest the head of the bed. As shown on the right hand side of FIG. 1, each second flap 32 is designed to be folded over on top of the associated first fastening means 22 and free ends 20 of flaps 18 once flaps 18 are secured to base 12 by first fastening means 22. Second flaps 32 are then secured in place by a second fastening means 34, comprising a button hole 36 in second flaps 32 and a button 38 (or other suitable fastening devices) secured to base 12 at the appropriate location.

Longitudinal edges 16 of base 12 preferable include a bridging member 40 sewn therein as shown in FIG. 2. Bridging member 40 is designed to reduce the sagging of base 12 and hence to help keep base 12 located above the person. Bridging member 40 is conveniently a small plastic or metallic band or rod which is resilient but which tends to hold its longitudinal shape.

In operation, bed restraint 10 functions in the following manner with a bed 50 such as depicted in FIG. 3. Bed 50 is a Fowler type, including upstanding sides 52 with a distinct top member 54 which is provided by the usual side rails of this type of bed. Of course, it will be appreciated that the present invention is usable with other types of beds, so long as a suitable top member is present. To mount bed restraint 10 to bed 50, bed restraint 10 must be opened up as shown in the left hand side of FIG. 1. In this position, it will be appreciated that flaps 18 are then passed through the associated apertures formed by the side rails and back over top member 54 to a position on top of base 12. Free ends 20 of flaps 18 are then attached to base 12 using first fastening means 22. Thereafter, second flap 32 is folded on top of free ends 20 and first fastening means 22, and second flap 32 is attached in place using second fastening means 34.

It will be appreciated that the person to be restrained in bed 50 is placed in bed 50 either before bed restraint 10 is attached in place or after only one side of bed restraint 10 is in place (so that bed restraint 10 can be folded out of the way of the person). Once in place (attached to both sides 52), bed restraint 10 spans the distance between sides 52 from the level of top member 54 so that base 12 remains high enough not to contact the person (with sagging of the center of base 12 reduced by use of bridging members 40). Thus, while in place, bed restraint 10 does not impede the normal sleeping movements of the person. However, base 12 is in position to impede the person from sitting up and hence from easily getting out of bed 50.

While bed restraint 10 is easily demounted from bed 50 by an attendant, it will be appreciated that this is not easily done by the person who is to be restrained and who has diminished capacities. Once in bed 50, the usual first step in removing bed restraint 10 is the undoing of second fastening means 34. However, as shown in FIG. 3, second fastening means 34 is located adjacent the longitudinal edge 16 which is furthest from the head of bed 50. Thus, the person can not easily reach button 38 of second fastening means 34 to undo it. And while it is only first fastening means 22 which actually need to be undone to allow the person to exit the bed easily, the person cannot easily do this while second flap 32 is in place (and due to diminished capacities, may not appreciate this).

Figure 5:
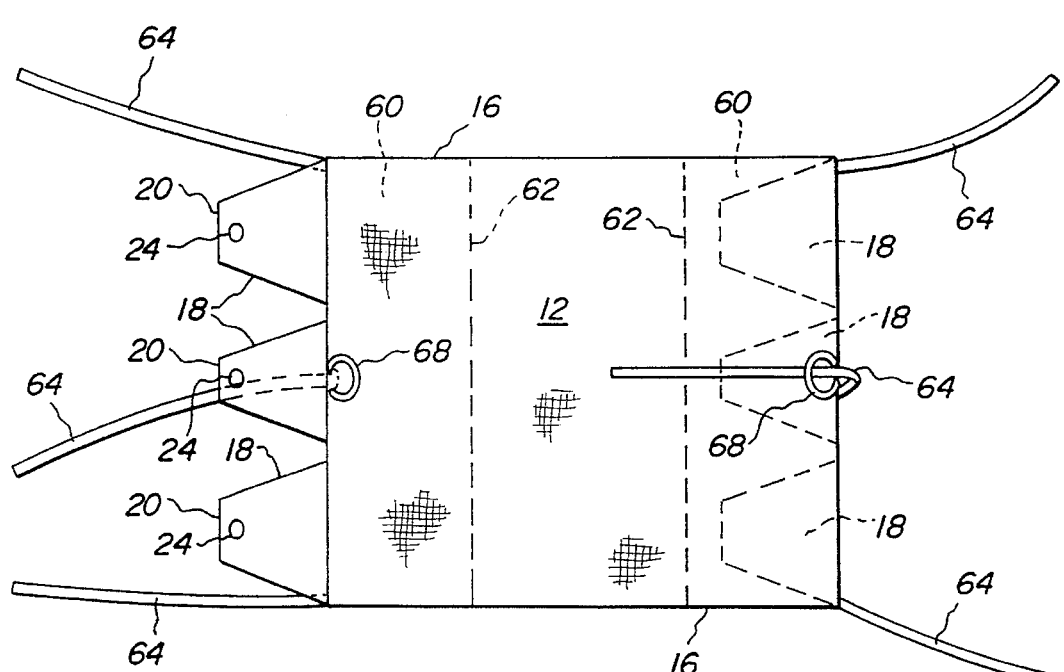
FIG. 5 is a bottom plan view of an alternative embodiment of the bed restraint of the present invention.

Alternatively, the pair of second flaps 32 shown in FIGS. 1 and 3 may be replaced by a pair of covering patches 60 forming pockets as shown in FIGS. 4 and 5 serving as the cover member 30. As in FIG. 1, bed restraint 10 includes an elongate base 12 having opposed lateral edges 14 and longitudinal edges 16, and flexible flaps 18 extending laterally from each lateral edge (shown extending on the left side of FIGS. 4 and 5 and folded over on the right side). These flaps 18 are attached to a bed as described in connection with FIG. 3. Covering patches 60 cover the buttons 26 at all times and cover the flaps 18 when they are fastened to the button 26, as seen on the right side of FIG. 4. The covering patches 60 are attached across the elongate base 12 as indicated at 62 and along a portion of the longitudinal edges 16 so as to form a pocket over respective first fastening means 22. Covering pockets 60 allow easy access to the first fastening means 22 for an attendant, but access is much more difficult for a person in the bed. The person in the bed will also have their view of how to fasten the flaps obfuscated the covering patches 60.

The covering patch 60 advantageously includes elongated, flexible strips 64 attached to the lateral, unattached edge 66 of the covering patch 60. These strips 64 are then used to close off the pocket formed by covering patch 60, thereby further restricting access to first fastening means 22 from the person to be restrained. In particular, the strips 64, either individually or any combination thereof may be looped through a ring 68 attached to the bottom surface of the base 12 and secured in a conventional manner, as can be seen in FIG. 5. Other suitable devices may be used for closing the pocket. Additional rings may used, each for securing a respective strip. Preferably, the base, the covering pocket and the strips are made of cloth and are stitched together, and the ring is made of metal.

While the present invention has been described with respect to exemplary embodiments thereof, it will be understood by those of ordinary skill in the art that variations and modifications can be effected within the scope and spirit of the invention.

I claim:

1. A bed restraint for helping to keep a person in bed where the bed includes upstanding sides having a distinct top member located, above a mattress comprising:

an elongate base having opposed lateral edges, said lateral edges extending longitudinally along respective ones of the top members of the sides of the bed;

at least one flexible flap extending laterally from each of said lateral edges and terminating at a free end, said flap being capable of extending around the top member of the associated side and back against said base with said free end in contact with said base;

a first fastening means for fastening said free end of each said flap to said base after said flap is passed around the top member so that said base is suspended above the mattress and helps to hold the person on the mattress; and a cover member for covering said first fastening means so that said first fastening means are hidden and not easily unfastened.

2. A bed restraint as claimed in claim 1 wherein there are three of said flexible flaps extending laterally from each of said lateral edges.

3. A bed restraint as claimed in claim 1 and further including a second fastening means for fastening said cover member to said base over said first fastening means.

4. A bed restraint as claimed in claim 3 wherein said base includes opposed longitudinal edges spanning said lateral edges; and wherein said cover member is a respective flexible second flap for each said first fastening means which is attached to an associated one of said longitudinal edges so as to be positionable over the respective said first fastening means; and wherein said second fastening means fastens said second flaps to said base.

5. A bed restraint as claimed in claim 3 wherein said second fastening means fastens said second flaps to said base at a position which is adjacent said longitudinal edge furthest from a head of the bed.

6. A bed restraint as claimed in claim 4 wherein each respective said second flap also covers the associated said free end when said second flap is fastened to said base.

7. A bed restraint as claimed in claim 3 wherein said base, said flaps, and said cover member are made of cloth and stitched together.

8. A bed restraint as claimed in claim 3 wherein said first fastening means and said second fastening means include a button and a button hole.

9. A bed restraint as claimed in claim 1 wherein said base includes opposed longitudinal edges spanning said lateral edges; and further including a bridging member located along said longitudinal edges to prevent the centers of said longitudinal edges from sagging excessively as said lateral edges are supported by the top members of the sides of the bed.

10. A bed restraint as claimed in claim 5 wherein said base, said first-mentioned flaps, and said second flaps are made of cloth and stitched together.

11. A bed restraint as claimed in claim 10 and further including a bridging member located along said longitudinal edges to prevent the centers of said longitudinal edges from sagging excessively as said lateral edges are supported by the top members of the sides of the bed.

12. A bed restraint as claimed in claim 11 wherein each respective said second flap also covers the associated said free end when said second flap is fastened to said base.

13. A bed restraint as claimed in claim 12 wherein said first fastening means and said second fastening means include a button attached to said base and a button hole in said free ends of said first-mentioned flaps and in said second flaps.

14. A bed restraint as claimed in claim 13 wherein there are three of said flexible flaps extending laterally from each of said lateral edges.

15. A bed restraint as claimed in claim 1 wherein said base includes opposed longitudinal edges spanning said lateral edges and said cover member is a flexible patch for each said first fastening means which is attached along a portion of each of said longitudinal edges and across said base so as to form a pocket over an associated first fastening means.

16. A bed restraint as claimed in claim 15, wherein said cover member further includes means for closing said pocket.

17. A bed restraint as claimed in claim 16, wherein said means for closing said pocket comprises flexible strips extending from a lateral unattached end of said patch and means for attaching said strips to a back side of said bed restraint opposite said cover member.

18. A bed restraint as claimed in claim 17, wherein said means for attaching comprises a ring attached to said back side.

19. A bed restraint as claimed in claim 17, wherein said flexible strips comprise three flexible strips, one at either lateral edge of said cover member and one at the middle of said patch.

20. A bed restraint for helping to keep a person in bed where the bed includes upstanding sides having a distinct top member located above a mattress comprising:
   an elongate base having opposed lateral edges, said lateral edges extending longitudinally along respective ones of the top members of the sides of the bed, said lateral edges extending only partially along the bed, leaving the bed uncovered by said elongate base for some longitudinal portion thereof;
   at least one flexible flap extending laterally from each of said lateral edges and terminating at a free end, said flap being capable of extending around the top member of the associated side and back against said base with said free end in contact with said base; and
   a first fastening means for fastening said free end of each said flap to said base after said flap is passed around the top member so that said base is suspended above the mattress and helps to hold the person on the mattress.

21. A bed restraint as claimed in claim 20, wherein there are three of said flexible flaps extending laterally from each of said lateral edges.

22. A bed restraint as claimed in claim 20, wherein said base includes opposed longitudinal edges spanning said lateral edges; and further including a bridging member located along said longitudinal edges to prevent the centers of said longitudinal edges from sagging excessively as said lateral edges are supported by the top members of the sides of the bed.

* * * * *

UNITED STATES PATENT AND TRADEMARK OFFICE
CERTIFICATE OF CORRECTION

PATENT NO. : 5,524,306
DATED : June 11, 1996
INVENTOR(S) : MORALES GEORGE

It is certified that error appears in the above-indentified patent and that said Letters Patent is hereby corrected as shown below:

On title page, item [19], should read --Morales George--

Item [75], should read --Hector Morales George--

Signed and Sealed this

Tenth Day of September, 1996

BRUCE LEHMAN

Attest:

Attesting Officer

Commissioner of Patents and Trademarks